(12) United States Patent
Berry (10) Patent No.: US 10,751,091 B1
(45) Date of Patent: Aug. 25, 2020

(54) TULIP HEAD AND COLLET FOR A POLY AXIAL SCREW

(71) Applicant: Bret Michael Berry, Tallahassee, FL (US)

(72) Inventor: Bret Michael Berry, Tallahassee, FL (US)

( * ) Notice: Subject to any disclaimer, the term of this patent is extended or adjusted under 35 U.S.C. 154(b) by 0 days.

(21) Appl. No.: 16/288,079

(22) Filed: Feb. 27, 2019

(51) Int. Cl.
*A61B 17/70* (2006.01)
*A61B 17/86* (2006.01)
*A61B 90/00* (2016.01)
*A61B 17/56* (2006.01)

(52) U.S. Cl.
CPC ...... *A61B 17/7032* (2013.01); *A61B 17/7035* (2013.01); *A61B 17/8605* (2013.01); *A61B 2017/564* (2013.01); *A61B 2090/037* (2016.02)

(58) Field of Classification Search
CPC .............. A61B 17/704; A61B 17/7041; A61B 17/7032; A61B 17/7037; Y10T 403/4614; Y10T 403/4608; Y10T 403/4617; Y10T 403/4611
See application file for complete search history.

(56) References Cited

U.S. PATENT DOCUMENTS

| | | | | |
|---|---|---|---|---|
| 5,910,142 A * | 6/1999 | Tatar | ..................... | A61B 17/704 606/272 |
| 5,938,663 A * | 8/1999 | Petreto | ............... | A61B 17/7041 606/278 |
| 7,316,684 B1 * | 1/2008 | Baccelli | ............. | A61B 17/7037 606/86 A |
| 8,277,485 B2 * | 10/2012 | Krishna | ............. | A61B 17/7034 606/246 |
| 9,456,852 B2 * | 10/2016 | Beyar | ................ | A61B 17/7076 |
| 9,498,254 B2 * | 11/2016 | Spratt | ................ | A61B 17/7032 |
| 2003/0004511 A1 * | 1/2003 | Ferree | ................ | A61B 17/7032 606/266 |
| 2003/0187439 A1 * | 10/2003 | Biedermann | ...... | A61B 17/7032 606/267 |
| 2004/0215190 A1 * | 10/2004 | Nguyen | ............. | A61B 17/7001 606/86 A |
| 2005/0267472 A1 * | 12/2005 | Biedermann | ...... | A61B 17/7032 606/308 |
| 2007/0043364 A1 * | 2/2007 | Cawley | ............. | A61B 17/7032 606/274 |
| 2007/0191842 A1 * | 8/2007 | Molz, IV | ........... | A61B 17/7037 606/86 A |
| 2008/0154308 A1 * | 6/2008 | Sherman | ............ | A61B 17/7008 606/265 |

(Continued)

*Primary Examiner* — Jan Christopher L Merene
(74) *Attorney, Agent, or Firm* — Ellenoff Grossman & Schole LLP; James M. Smedley; Alex Korona (57) ABSTRACT

The present invention generally relates to connectors that connect bone screws with fusion rods for use in stabilizing surgery such as spinal fusion surgery, and to bone screw systems comprising such connectors. In particular, the present invention relates to poly axial screw systems configured to attach the poly axial tulip head after the bone screw has been implanted. Furthermore, embodiments of the present invention relate to tulip connectors which have a hinged joint and a collet that are configured to rotatably and pivotably lock onto the ball head of a poly axial screw shaft. The poly axial tulip head features a collet which can attach to the rod prior to insertion onto the bone screw. The tulip head and rod are then affixed to the bone screw with a nut.

19 Claims, 10 Drawing Sheets

(56) References Cited

U.S. PATENT DOCUMENTS

| | | | |
|---|---|---|---|
| 2008/0234756 A1* | 9/2008 | Sutcliffe | A61B 17/7037 606/308 |
| 2008/0312655 A1* | 12/2008 | Kirschman | A61B 17/7032 606/308 |
| 2009/0005813 A1* | 1/2009 | Crall | A61B 17/7035 606/246 |

* cited by examiner

TULIP HEAD AND COLLET FOR A POLY AXIAL SCREW

FIELD OF THE INVENTION

The present invention generally relates to connectors that connect bone screws with fusion rods for use in stabilizing surgery such as spinal fusion surgery, and to bone screw systems comprising such connectors. In particular, the present invention relates to poly axial screw systems configured to provide a stable but adjustable angular placement. Furthermore, embodiments of the present invention relate to tulip connectors which have a head and a collet, that are configured to rotatably and pivotably lock onto the ball head of a poly axial screw shaft which are detachable from the screw shaft, and to methods of attaching said tulip head to the screw shaft.

BACKGROUND OF THE INVENTION

Poly axial screws are used e.g. for fixation of a patient's spinal column in spinal surgery that is performed to fuse individual spinal vertebrae. A screw shaft is inserted into the bone, e.g. the pedicle of each vertebrae to be fused, and a fusion rod is attached by connectors mounted on the screw shaft to multiple screws, to form a supporting structure that fixates the vertebrae and prevents movement. Over time, lack of movement as well as bone transplants implanted at the surgery site for this purpose allows bone to grow and permanently fuse the bones of the vertebrae after surgery.

Many different models exist for pedicle screws which generally have a screw shaft and a U-shaped connector that connects the screw to a fusion rod. In mono axial screws, the head of the screw can be aligned with the position of the rod only to a limited extent, necessitating complicated bending to correct the angle. Poly axial screws generally have a screw shaft with ball head and the U-shaped connector or tulip rotatably and pivotably coupled thereto.

While poly axial screws allow more flexibility in positioning of the screw shafts and fusion rods, they often lack the rigidity or stability required to achieve and maintain an accurate angular placement during surgery, may be difficult to connect to a fusion rod, and/or create even more bulky structures that interfere with surgery, causing more tissue damage and/or require larger incisions.

Typically, the parts of a poly axial screw are configured for pre-assembly before implantation, the shape, size or number of their parts making them complicated to assemble, bulky, and/or are difficult to implant. The resulting system may lack flexibility or rigidity or both. The bulk of the poly axial screw system can also complicate surgery before and after implanting of the screws, as it may require larger or different incisions and more soft tissue may have to be removed, thus complicating surgery and prolonging healing times. Also the bulky structure, once implanted, may interfere with the view of the surgeon during the ongoing surgery, e.g. during placement of bone implants, and also if discs (between the vertebrae) are removed and replaced with interbodies, as is often the case (e.g. herniated discs). Further the bulk may interfere with imaging techniques to determine correct placement of the screw system itself, or of the placement of related therapeutic components, such as interbody transplants and positioning tools.

In some systems, threaded fasteners are used to secure the rods to the connectors. The rods can be provisionally held in position by loosely tightening the fasteners, and after desired adjustments are made, the fasteners can be further tightened by torque and fixated into a final position. Such procedures typically requires a torque wrench or similar device, and to prevent torque from being transferred to the patient, require an anti-torque device in parallel. The effective use of both devices requires skill and is dependent upon the strength and experience of the surgeon. The provisionally loosely tightening typically results in unpredictable inconsistent results with regards to adjustability—the fastener may have been tightened to little, resulting in the correct position being lost, e.g. as the structure shifts in the course of the ongoing surgery as the structure or the surrounding bone and tissue is manipulated, or the fastener may have been tightened too much, so adjustments cannot be made without first loosening it again, applying unnecessary torque or requiring use of an anti-torque device.

Therefore, there is a need in the art for a poly axial screw system that avoids bulk, is easily and quickly assembled, has flexible assembly options, is easily positioned, provides a sufficient and consistent degree of rigidity to retain its preliminary axial position after assembly, and is easily and quickly adjusted before fixation into the final position. Also, there is a need in the art for a system that avoids excessive torque, in particular when adjusting repeatedly before fixation. These and other features and advantages of the present invention will be explained and become apparent to one skilled in the art through the following description of the invention.

SUMMARY OF THE INVENTION

The present invention generally relates to connectors that connect bone screws with fusion rods for use in stabilizing surgery such as spinal fusion surgery, and to bone screw systems comprising such connectors. In particular, the present invention relates to poly axial screw systems configured to provide a stable but adjustable angular placement. Furthermore, embodiments of the present invention relate to tulip connectors which have a head and a collet, which are configured to engage with a bone screw while holding onto a rod.

According to an embodiment of the present invention, provided is a tulip for connecting a fusion rod to a poly axial screw, the tulip comprising a head and a collet configured for assembly onto a ball head of a poly axial screw shaft during spinal fusion surgery; wherein the collet is configured with an upper base with an upper joint part and two saddle horns; wherein the saddle, its base and its two saddle horns are configured to connect with a fusion rod, with the length of the rod placed across the saddle base, the two horns cradling part of the sides of the rod; wherein the joint is configured with an open and a closed position; wherein the tulip head comprises a first side and a second side, collectively creating two chambers, an upper chamber and a lower chamber; wherein the lower chamber is wider than the upper chamber, and the lower chamber is configured to fit the ball head of the poly axial screw shaft; wherein the lower and upper chambers are configured to fit the collet around the ball head of the poly axial screw shaft; wherein the upper chamber of the tulip head is configured to engage with a fastener, thus allowing fixation of the poly axial screw to the fusion rod in their final positions.

According to an embodiment of the present invention, provided is a system for connecting a fusion rod to a poly axial screw, the system comprising a tulip head, a collet, and a screw shaft with ball head, wherein the poly axial screw shaft is configured for implantation without the tulip; wherein the collet is configured with a lower saddle part with an upper base and two saddle horns and an upper joint part; wherein the saddle, its base and its two saddle horns are configured to connect to a fusion rod, with the length of the rod placed across the saddle base, the two horns cradling part of the sides of the rod; wherein the joint is configured with an open and a closed position; wherein the tulip head comprises two chambers, an upper chamber and a lower chamber; wherein the lower chamber is wider than the upper chamber, and the lower chamber is configured to fit the ball head of the poly axial screw shaft; wherein the upper and lower chambers are configured to fit the collet; wherein the top part of the tulip head is configured to engage with a fastener to allow fixation of the connection to a fusion rod in its final position.

According to an embodiment of the present invention, provided is a system comprising a tulip head, a collet and a screw shaft with a ball head as described herein, additionally comprising a fusion rod.

According to embodiments of the present invention, a bone screw may be implanted into the vertebrae. Once the bone screw has been implanted, a tulip head and a collet, engaged with a rod, may be attached to the top of the bone screw. Finally, a tulip fastener may be engaged with the top of the tulip head to secure the construct.

According to an embodiment of the present invention, provided is a tulip head and collet for connecting a fusion rod to a poly axial screw, the tulip head comprising a hinged joint and a collet configured for assembly onto a ball head of a poly axial screw shaft during spinal fusion surgery; wherein the collet is configured with a lower saddle part and two saddle horns and a upper hinge joint part, the top of the collet having a hole through which a hinge pin may intersect, engaging the collet with the tulip head; wherein the saddle and its two saddle horns are configured to connect to a fusion rod, with the length of the rod placed across the saddle base, the two horns cradling part of the sides of the rod; wherein the joint is configured with an open and a closed position, and comprises a plurality of joint members that are configured to be separated in the open position, and to make closer contact with each other in the closed position.

According to an embodiment of the present invention, provided is a tulip head compromised of two sides engaged by a joint. The top of each side is attached to the other by a hinge joint. The collet may also be connected at this hinge joint. In some embodiments, a tulip fastener may engage with the tulip head. In some embodiments, the upper section of the tulip head includes a threaded portion, corresponding to a threaded portion along an interior portion of a tulip fastener, for the fastening of the tulip fastener to the tulip head. In some embodiments, the exterior portion of the upper section of each side of the tulip head includes a partial spiral wedge having a divot at one end. Each spiral wedge may be deeper at the edge of the tulip head and shallower at the middle of the tulip head. In an exemplary embodiment, the tulip fastener may be placed onto the tulip head such that the locking protrusions on the tulip fastener may easily slide into the deeper portions or divots at one end of the spiral wedges. As the tulip fastener is twisted, the locking protrusions become pressed against the shallow portions of the spiral wedges to secure the tulip fastener to the tulip head.

According to an embodiment of the present invention, provided is a tulip head as described herein wherein the interior portion of the lower part of each tulip head side contains a concave portion. The concave portion is provided to receive the round portion of a bone screw. When the tulip fastener is engaged with the tulip head in an unlocked position, the concave portion of the tulip fits snugly onto the round portion of the bone screw, while still allowing for the tulip head to pivot and rotate about the head of the bone screw. As the tulip fastener tightens the two sides of the tulip head, the concave portions form a friction fit onto the round portion of the bone screw. Furthermore, as the tulip fastener becomes fastened to the tulip head, the tulip fastener presses down upon the rod, forcing the rod out of the saddle of the collet, and onto the head of the bone screw. This action locks the rod into position in addition to forcing the head of the bone screw against the interior concave portion of the tulip head.

According to an embodiment of the present invention, provided is a tulip as described herein wherein the tulip head is made of a rigid material, and the tulip collet is made of a less rigid material.

According to an embodiment of the present invention, provided is a tulip as described herein wherein the tulip head is made of a rigid material including one or more of cobalt-chrome, cobalt-chrome alloy, titanium, titanium alloy, and the tulip collet is made of a less rigid material.

According to an embodiment of the present invention, provided is a tulip as described herein wherein the tulip head is made of one or more of cobalt-chrome, and cobalt-chrome alloy, optionally coated with one or more of titanium and titanium alloy, and the tulip collet is made of one or more of titanium and titanium alloy.

According to an embodiment of the present invention, provided is a system comprising a tulip head, tulip collet and screw shaft with ball head as described herein, additionally comprising a fusion rod.

The foregoing summary of the present invention with the preferred embodiments should not be construed to limit the scope of the invention. It should be understood and obvious to one skilled in the art that the embodiments of the invention thus described may be further modified without departing from the spirit and scope of the invention. Other features and advantages of the invention will be apparent from the following specification taken in conjunction with the following drawings. While many materials and methods of design have been attempted, a number of drawback and limitations prevent an optimal design.

BRIEF DESCRIPTION OF THE DRAWINGS

Accompanying this written specification is a collection of drawings of exemplary embodiments of the present invention. One of ordinary skill in the art would appreciate that these are merely exemplary embodiments, and additional and alternative embodiments may exist and still be within the spirit of the invention as described herein.

DETAILED DESCRIPTION

The present invention generally relates to connectors that connect poly axial screws with fusion rods for use in spinal fusion surgery, and to poly axial screw systems comprising such connectors. In particular, the present invention relates to poly axial screw systems configured to provide an adjustably locked preliminary, and a fixated final position for the tulip with fusion rod.

Figure 1:
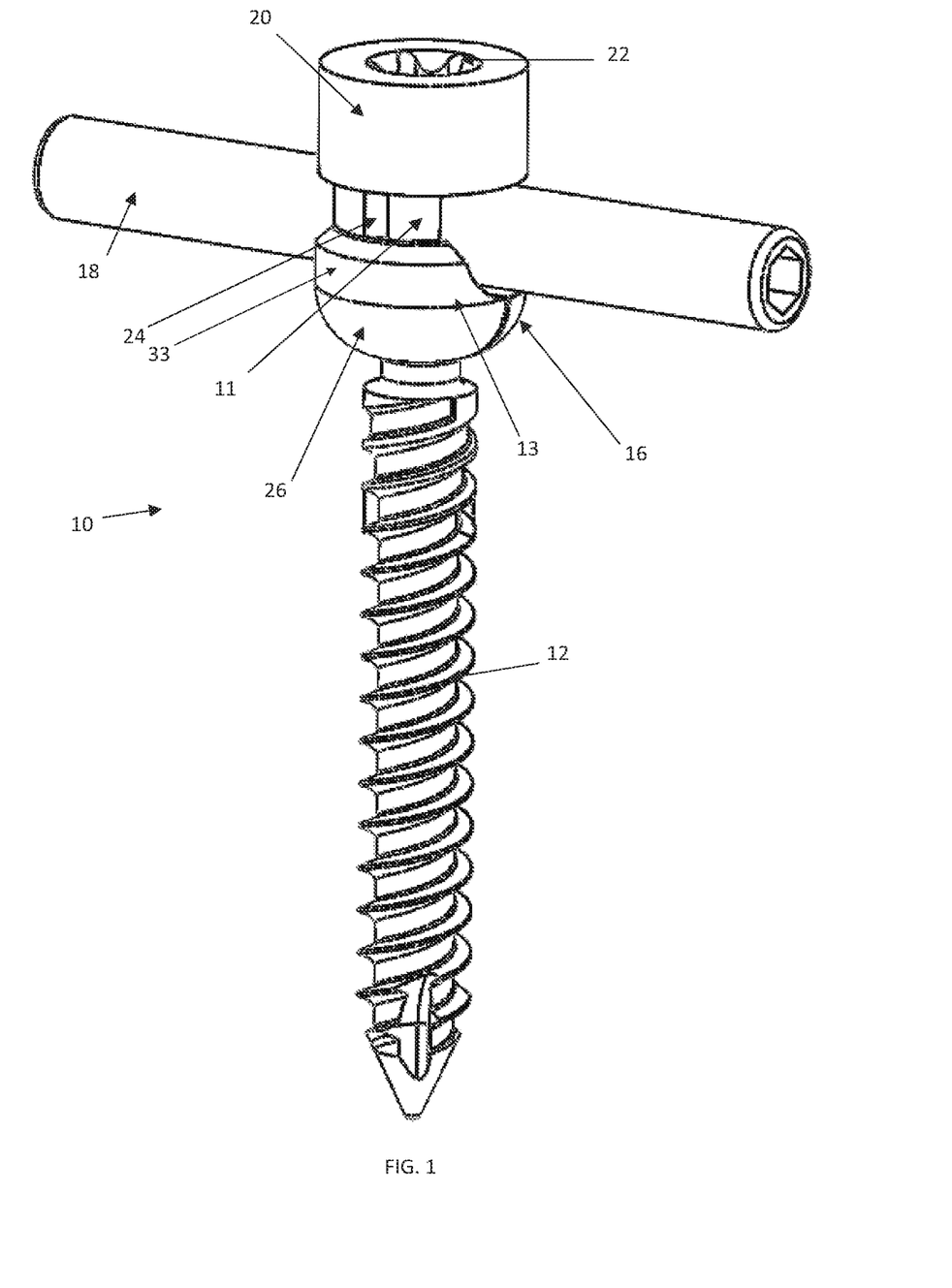
FIG. 1 is a perspective view of an assembled poly axial screw system with a tulip head connected to a fusion rod and a tulip fastener attached, in accordance with an embodiment of the present invention.

The poly axial screw system of the present invention is configured for assembly during surgery, after implantation of the screw shaft (see FIG. 1). The system comprises a two-part tulip connector with a head and a collet (see FIG. 2) that is adapted to lock onto the ball head of the implanted screw shaft.

According to embodiments of the present invention, the tulip head and collet are configured with a loose and a locked position when engaging with each other and with the ball head of the screw shaft during assembly of the poly axial screw system. In the loose position, the tulip head loosely fits an implanted screw shaft and the collet holds the fusion rod, the fusion rod connecting with the upper base and the two saddle horns of the collet. In the locked position, the tulip head tightly fits around the ball head, providing sufficient rigidity and stability to reliably keep the position the tulip head in place in during surgery (safeguarding against the occasional inadvertent touch or bump by the surgeon's hands, tools, moving tissue, bone structure, implants etc.) and the saddle horns of the collet hold the fusion rod. The tulip head may remain pivotably and rotatably adjustable by manual force. After all adjustments have been made, a fastener may be utilized to fixate the poly axial screw system. In the locked position, the fastener presses against the fusion rod placed in the collet and pushes the fusion rod downwards until the rod tightly sits on the ball head of the screw shaft, while the sides of the fusion rod are held across the collet in the saddle horns.

According to an embodiment of the present invention, the collet may be configured with a lower section or saddle and an upper section or joint.

Figure 4:
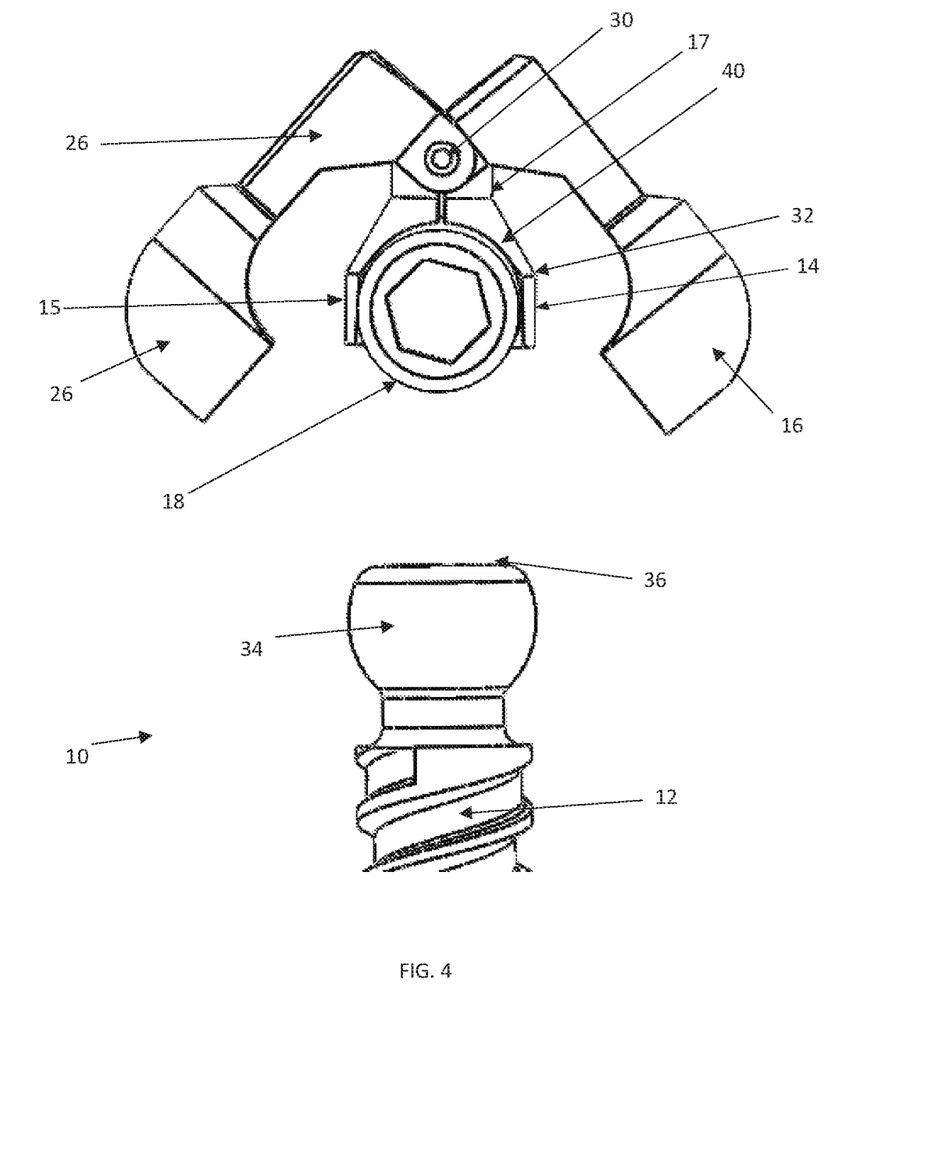
FIG. 4 is a side view of an unassembled poly axial screw system with a tulip head connected to a fusion rod, in accordance with an embodiment of the present invention.

According to an embodiment of the present invention, the saddle of the collet has an upper base and two saddle horns, and is configured to accept the fusion rod across the base and in between its two saddle horns when the tulip is in its open position (see FIG. 4).

Figures 5, 6:
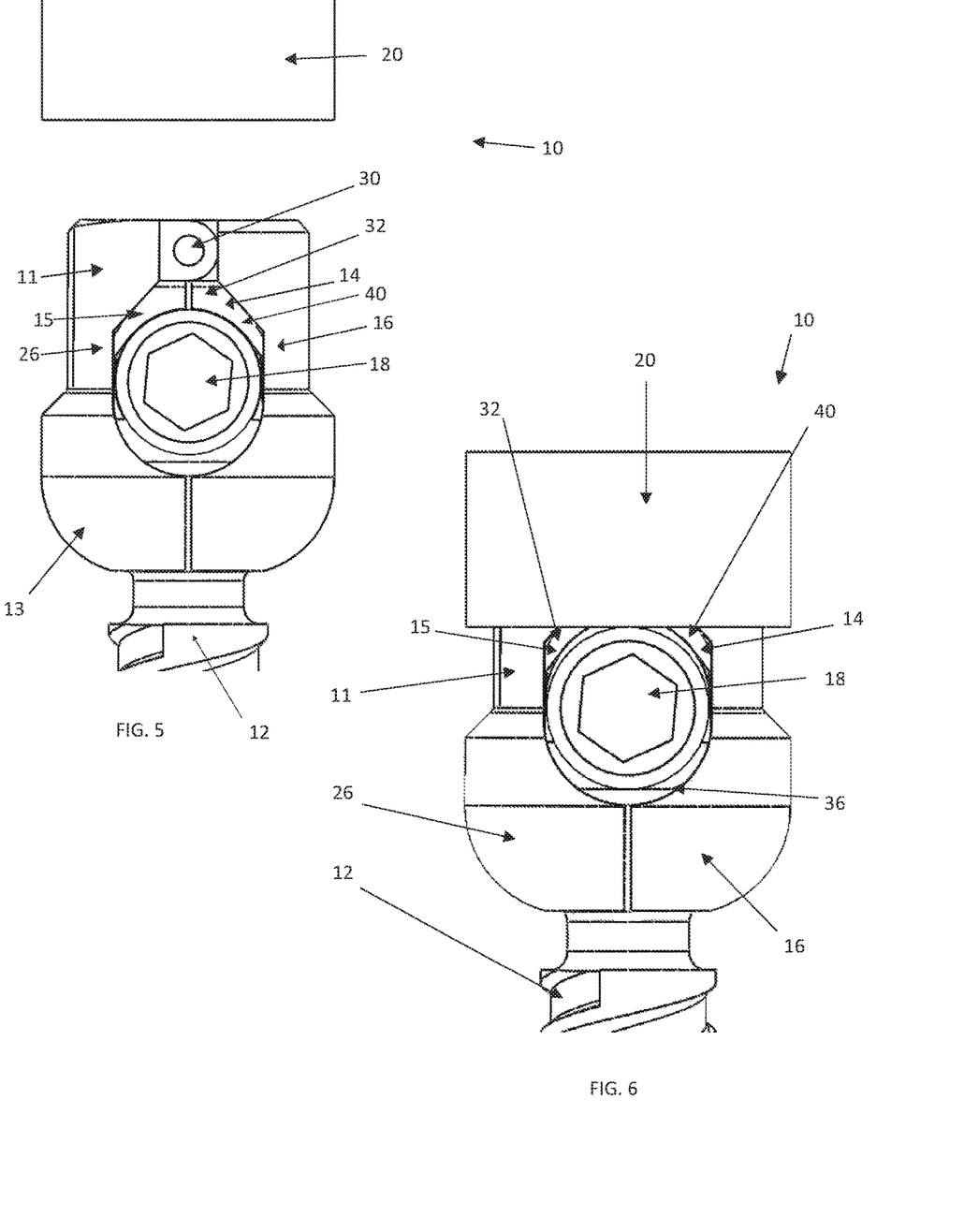
FIG. 5 is a side view of an assembled poly axial screw system with a tulip head connected to a fusion rod and a tulip fastener detached, in accordance with an embodiment of the present invention.
FIG. 6 is a side view of an assembled poly axial screw system with a tulip head connected to a fusion rod and a tulip fastener attached, in accordance with an embodiment of the present invention.

In embodiments of the invention, the tulip may comprise three separate parts, a tulip head which has an open and closed position, a tulip collet, and a tulip fastener to lock the tulip in place when the fastener is pushed or twisted down onto the upper chamber of the tulip head, securing the tulip head into its closed position (see FIGS. 5 and 6).

In embodiments of the invention, the joint of the collet may be configured with an open and a closed position. In the open position, the collet is configured to accept the fusion rod in a loose fit. In the closed position, a tighter fit of the fusion rod is achieved, thus providing sufficient stability but allowing adjustment of position.

According to an embodiment of the present invention, the tulip head may be configured to accommodate the collet in an open position in which the collet provides a loose fit of the fusion rod and the tulip head provides a loose fit around the ball head. In some embodiments, the tulip head may be configured with a means to fixate the fusion rod into the final position. In some embodiments, a tulip fastener facilitates the transformation from the open position into a locked position in which the tulip head provides a tight fit around the ball head of a poly axial screw.

In embodiments of the invention, the tulip head may be configured with two chambers: an upper chamber and a lower chamber, with an optional threaded top section to achieve fixation into the final position using a tulip fastener.

In embodiments of the invention, the lower chamber may configured to accommodate a ball head of a screw. The upper chamber may be configured to fit the collet with a portion of the fusion rod placed across the collet. Thus, the tulip head may be configured to fit over and loosely cradle the ball head of the screw shaft in the lower chamber. As the tulip fastener is pushed or twisted downwards onto the lower chamber of the tulip head, manually or by a tulip assembly tool, the fusion rod is pushed down from the upper base of the collet and onto the ball head of the poly axial screw while the saddle horns hold the sides of the rod and the concave portion of the lower chamber tightens over the ball head.

In embodiments of the invention, the upper chamber of the tulip head may be configured with an upper joint. The upper joint engages the top of the first side of the tulip with the top of the second side of the tulip. The tulip is in its open position when the two sides of the lower chamber of the tulip are spread further apart than the two sides of the upper chamber. The tulip may be placed in its closed position by bringing the first side of the lower chamber closer to the second side of the lower chamber and connecting the tulip fastener to the upper chamber of the tulip head. As the tulip fastener is pushed or twisted downwards to reposition the tulip into the locked position, the fastener forces the two sides of the upper chamber of the tulip head closer together, and pushes the fusion rod placed in the upper saddle of the collet downwards so that it is repositioned to sit tightly between the tulip fastener and the ball head of a poly axial screw (see FIGS. 4 and 6). The ball head may include a rim to support a bottom side of the fusion rod.

According to an embodiment of the invention, the upper portion of the tulip fastener may be configured with a docking area to allow a tulip assembly tool to grab the tulip head during assembly of the tulip onto the ball head and for achieving the closed position. The docking area may be at the outer sides or upper rim of the tulip head, and may be configured as cutouts, protrusions or a rough surface area that matches the outer hooks of the tulip assembly tool and/or allows it to grab the tulip head by providing sufficient friction for a secure hold. The docking area cutouts or protrusions may have any suitable shape that fits correspondingly shaped hooks in the assembly tool. For example, slots or holes to fit the contacting hook area that may be line or pin shaped. Any matching configurations that allow the hooks to securely grab the docking area may be used, as will be apparent to a person of ordinary skill in the art.

Fasteners to achieve a final fixated position of the poly axial screw and the fusion rod may be locking nuts or caps having threaded interiors, corresponding to a threaded exterior of the top portion of a tulip head for fastening. However, alternative fasteners may be used, and the poly axial screw system may be configured accordingly, for example for fixation with any suitable fastener that is of a biocompatible material and sufficient durability, including e.g. bolt and nut, rivet, latches, hooks, expanding anchors, or biocompatible adhesives, as will be apparent to a person skilled in the art.

According to embodiments of the invention, the poly axial screw system may be assembled with or without a specialized tool.

The poly axial screw parts (tulip head, tulip collet, tulip fastener and screw shaft with ball head) may be made from various biocompatible materials suitable for implantation into the mammalian or human body, including various metals, metal alloys and their mixtures, coated metals or coated metal alloys, polymers, and oxide ceramics, as will be apparent to a person of ordinary skill in the art. These may include, for example, stainless steel, pure titanium standard, titanium alloy, TAV (Ti6Al4V), TAN (Ti6AL7Nb), TAN standard (titanium-coated cobalt-chrome), TAN new finish (titanium-coated cobalt-chrome), cobalt-chrome, cobalt-chrome alloys, cobalt-chrome/titanium coating, cobalt-chrome/zirconium/titanium coating, cobalt-chrome-molybdane, zirconium, aluminum, vanadium, vitallium, plastic polymers such as ultra-high-molecular weight-polyethylene (UHMWP), polyetheretherketone (PEEK), polyurethanes and composites including composites containing carbon fiber, polycarbonate urethane, natural or synthetic elastomers such as polyisoprene (natural rubber), synthetic polymers, copolymers, and thermoplastic elastomers, for example, polyurethane elastomers such as polycarbonate-urethane elastomer, other polymers and oxide ceramics. Titanium and its alloys may be used for superior bone on-growth compared to other metals and metals/metal alloys.

The poly axial screw parts may be made from one material, or a combination of one or more different materials (including differently treated materials that have different characteristics). Different materials may be used to form any or all of the poly axial screw parts based upon the desired characteristics such as strength, hardness, rigidity, resilience and elasticity of the specific part. For example, the tulip head and fastener may be formed from cobalt-chrome, and the collet and screw shaft with ball head may be formed from titanium or a titanium alloy. If different metal or metal alloys are combined, especially when in direct contact, metal combinations that can promote corrosion should be avoided, or optionally suitable coatings may be used, as will be apparent to the person of ordinary skill in the art.

The tulip collet is typically made from less rigid materials that are more easily deformable than the remaining poly axial screw parts (i.e. tulip head, tulip fastener, and screw shaft with ball head).

The screw shaft is threaded, typically with a V-thread, but other thread types with different thread angles may be used, for example, buttress or square threads. The screw shaft and may optionally comprise additional features such as radial holes, depending on the particular application and patient, e.g. to increase pull-out strength, as will be apparent to a person of ordinary skill in the art. Optionally, the screw shaft may be cannulated, to allow a guide wire to pass through for placement, e.g. a fluorescent wire for imaging technique-assisted placement.

The poly axial screws parts optionally may be surface treated with various methods according to the material used, as will be apparent to a person of ordinary skill in the art. Surface treatment results in a rougher surface that typically promotes osseointegration. Various methods are known and may result in 0.05 µm-0.5 µm surface roughness, e.g. 0.15 µm-0.4 µm or 0.2 µm-0.35 µm. For example, a steel surface may be electropolished to a surface roughness of about 0.2 µm to about 0.24 µm, e.g. about 0.22 µm; a cobalt chrome surface may be treated by passivation to achieve the same surface roughness; a TAN surface may be prepared by electrochemical anodisation to a surface roughness of about 0.3 µm-0.34 µm, e.g. about 0.32 µm; and a TAN-new-finish may be additionally polished to a surface roughness of ca. 0.28 µm).

The embodiments of the present invention may be used in various types of bone-stabilizing surgery, including but not limited to spinal surgery, in particular spinal fusion surgery. For example, embodiments of the present invention may be useful for posterolateral fusion, interbody fusion, Posterior lumbar interbody fusion (PLIF, the disc is accessed from a posterior position and includes removing the disc between two vertebrae and inserting bone into the space created between the two vertebral bodies), Posterolateral gutter fusion (the procedure is done through the back), Anterior lumbar interbody fusion (ALIF, the disc is accessed from an anterior abdominal incision and includes removing the disc between two vertebrae and inserting bone into the space created between the two vertebral bodies), Anterior/posterior spinal fusion, Transforaminal lumbar interbody fusion (TLIF, the disc is accessed from a posterior incision on one side of the spine), Extreme Lateral Interbody Fusion (XLIF, an interbody fusion in which the disc is accessed laterally), Transpsoas interbody fusion (DLIF or XLIF, the disc is accessed from an incision through the psoas muscle on one side of the spine), and Oblique lateral lumbar interbody fusion (OLLIF, the disc is accessed from an incision through the psoas muscle obliquely).

Figure 2:
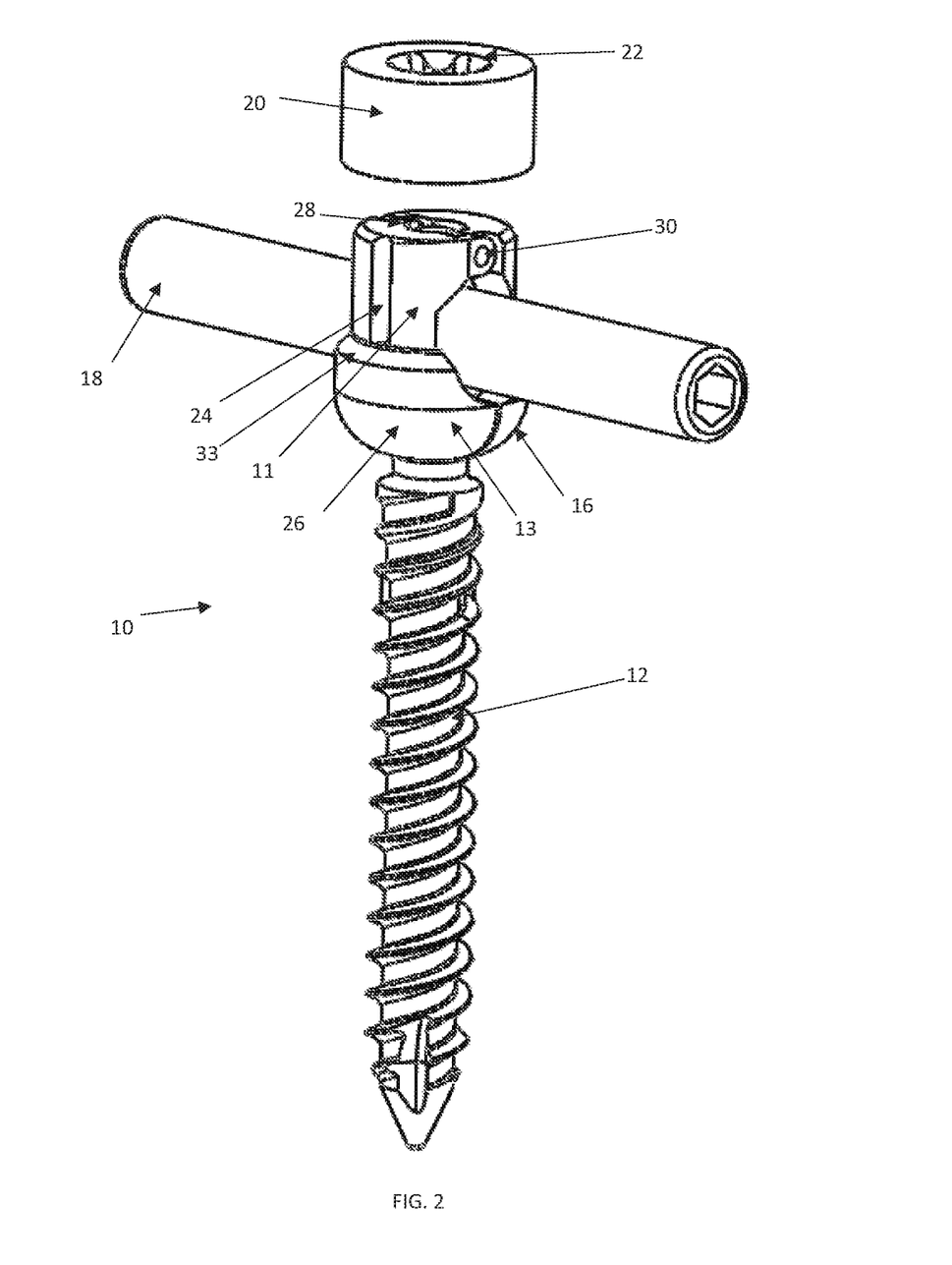
FIG. 2 is a perspective view of an assembled poly axial screw system with a tulip head connected to a fusion rod and a tulip fastener detached, in accordance with an embodiment of the present invention.
Figure 3:
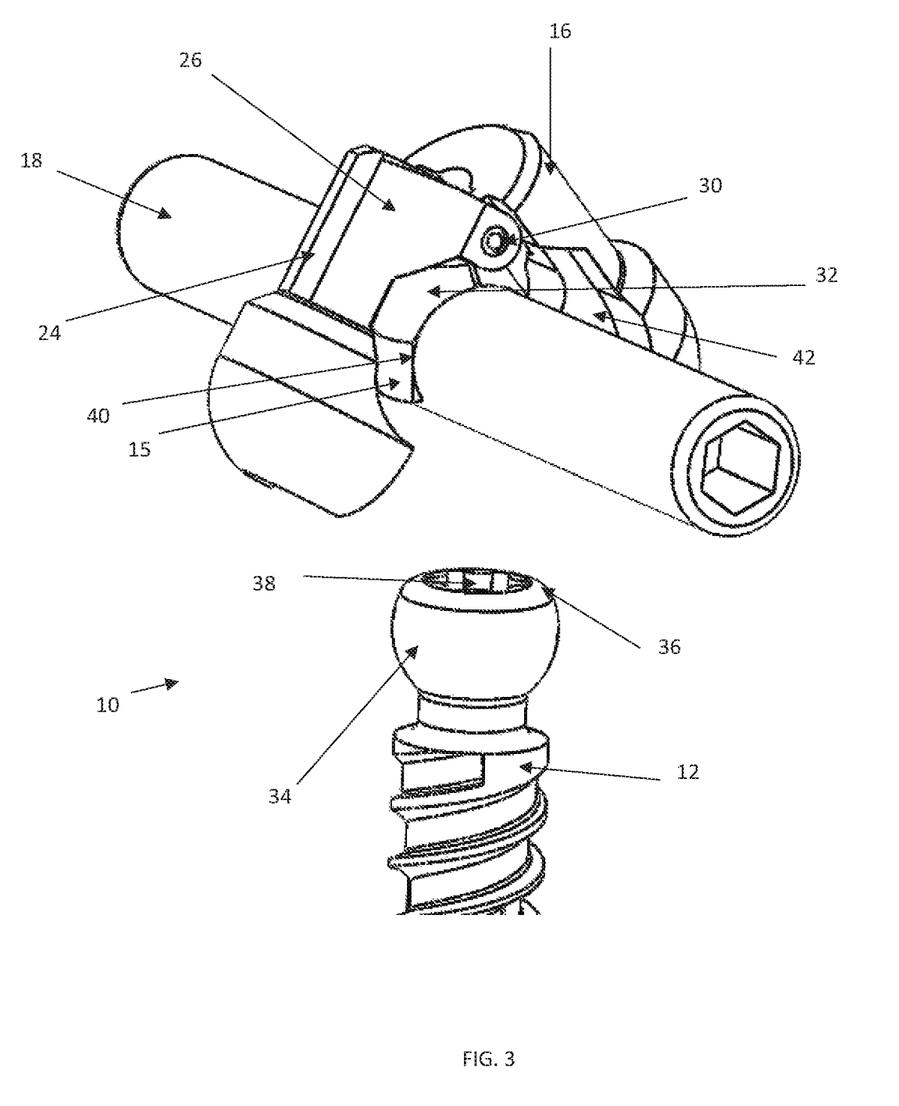
FIG. 3 is a perspective view of an unassembled poly axial screw system with a tulip head connected to a fusion rod, in accordance with an embodiment of the present invention.

FIGS. 1-16 generally show a poly axial screw system 10 in accordance with an embodiment of the present invention. As shown in FIGS. 1-3, in some embodiments, the poly axial screw system 10 of the present invention has a tulip head 33, a tulip collet 32, a fusion rod 18, and a screw 12 having a ball head 34. FIGS. 1-8 generally show a poly axial screw system 10 with a tulip head 33 having partial spiral wedge portions 19 and 21 for engagement with locking protrusions 28 and 29 on a tulip fastener 20. FIGS. 9-16 generally show a poly axial screw system 10 with a tulip head 33 having a threaded portion 25 on the exterior portion of the upper chamber 11 for engagement with a corresponding threaded portion 35 along an interior portion of the fastener 20.

A shown in FIGS. 1-8, provided is a tulip head 33 and collet 32 for connecting a fusion rod 18 to a poly axial screw 12, the tulip head 33 comprising an upper chamber 11, a lower chamber 13, a joint 30 and a collet 32 configured for assembly onto a ball head 34 of a poly axial screw 12 during spinal fusion surgery; wherein the collet 32 is configured with a saddle 40, comprised of an upper base 17, two saddle horns 14 and 15, and an upper hinge joint 30; wherein the upper base 17 and the two saddle horns 14 and 15 are configured to connect to a fusion rod 18, with the length of the rod 18 placed across the upper base 17 of the saddle 40, the two saddle horns 14 and 15 cradling part of the sides of the rod 18; wherein the joint 30 is configured with an open and a closed position, and comprises a plurality of joint members that are configured to be separated in the open position (FIG. 4), and to make closer contact with each other in the closed position (FIG. 5). In some embodiments, the upper base 17 has a hole through which a hinge pin intersects, engaging the collet 32 with the tulip head 33.

As shown in FIGS. 4-6, provided is a tulip head 33 in accordance with an embodiment of the present invention, compromised of a first side 16 and a second side 26. In some embodiments, the upper chamber 11 comprises a joint 30, engaging the top portion of the first side 16 with the top portion of the second side 26. The first side 16 and the second side 26 are rotatable about the axis of the joint 30, to enable the tulip head 33 to transform between an open position (FIG. 4) and a closed position (FIG. 5). A collet 32 may also be engaged with the joint 30.

Figure 7:
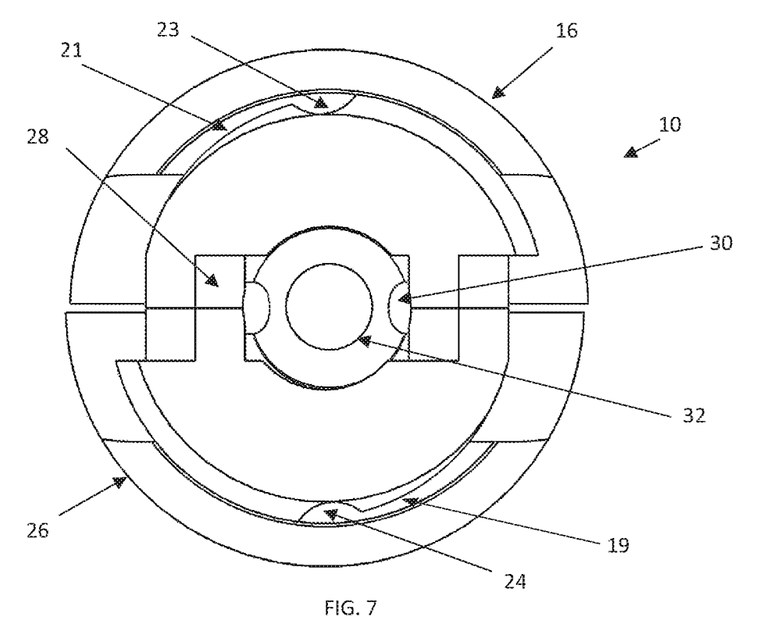
FIG. 7 is a top view of a tulip head of a poly axial screw system, in accordance with an embodiment of the present invention.
Figure 8:
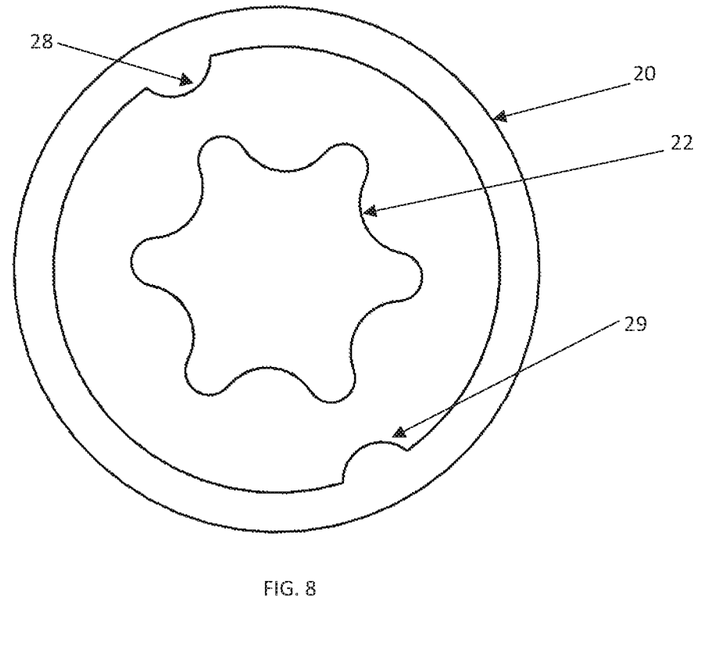
FIG. 8 is a bottom view of a tulip fastener, in accordance with an embodiment of the present invention.
Figure 9:
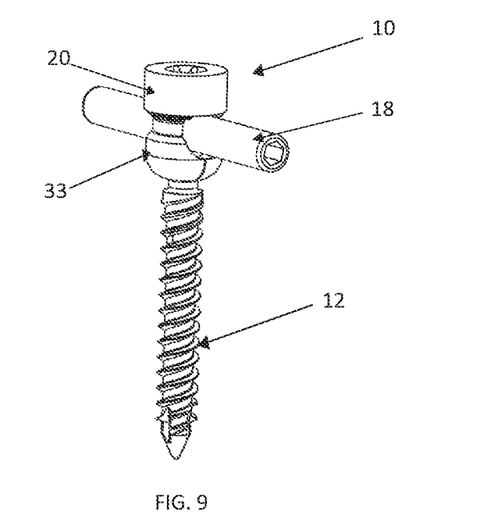
FIG. 9 is a perspective view of an assembled poly axial screw system with a threaded tulip head connected to a fusion rod and a tulip fastener attached, in accordance with an embodiment of the present invention.
Figure 10:
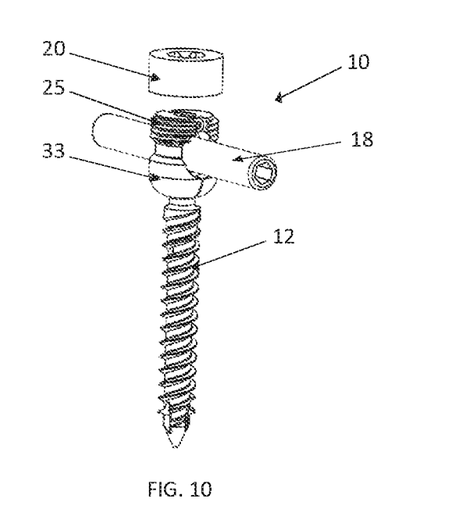
FIG. 10 is a perspective view of an assembled poly axial screw system with a threaded tulip head connected to a fusion rod and a tulip fastener detached, in accordance with an embodiment of the present invention.
Figure 11:
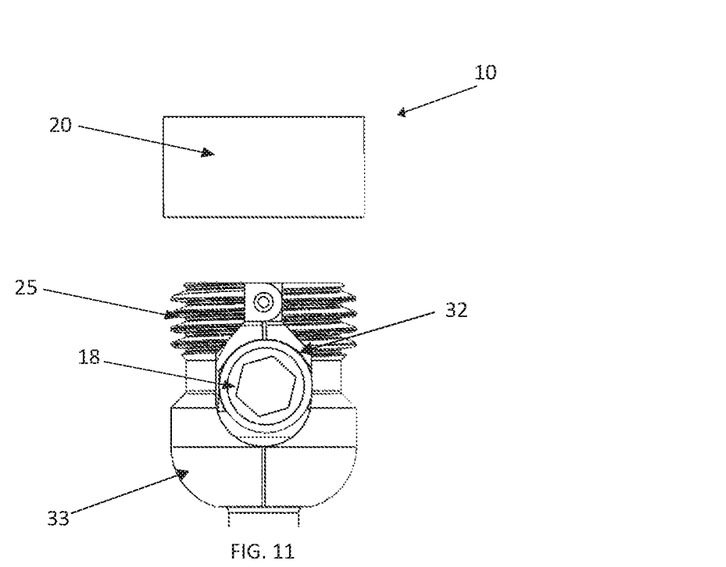
FIG. 11 is a side view of an assembled poly axial screw system with a threaded tulip head connected to a fusion rod and a tulip fastener detached, in accordance with an embodiment of the present invention.
Figure 12:
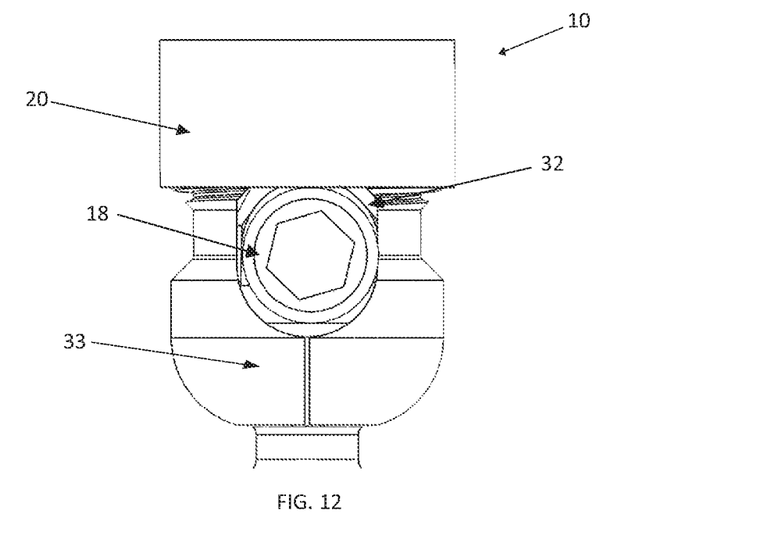
FIG. 12 is a side view of an assembled poly axial screw system with a threaded tulip head connected to a fusion rod and a tulip fastener attached, in accordance with an embodiment of the present invention.
Figure 13:
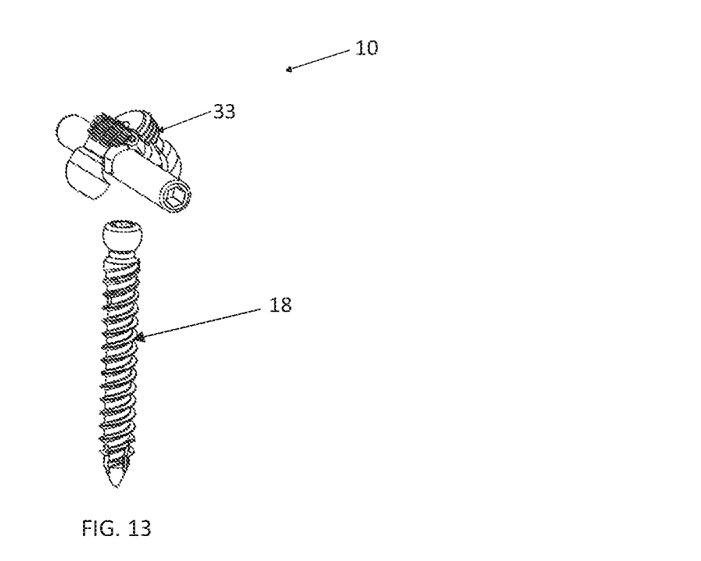
FIG. 13 is a perspective view of an unassembled poly axial screw system with a threaded tulip head connected to a fusion rod and a tulip fastener detached, in accordance with an embodiment of the present invention.
Figure 14:
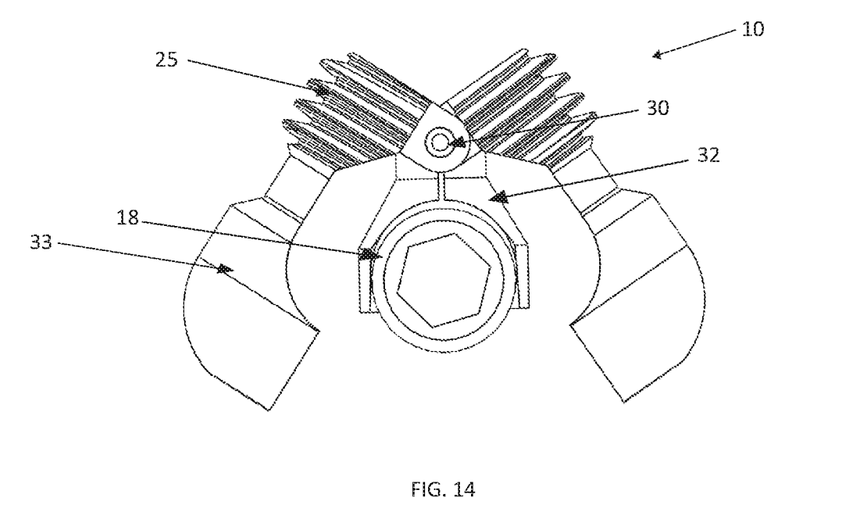
FIG. 14 is a side view of an unassembled threaded tulip head connected to a fusion rod, in accordance with an embodiment of the present invention.
Figure 15:
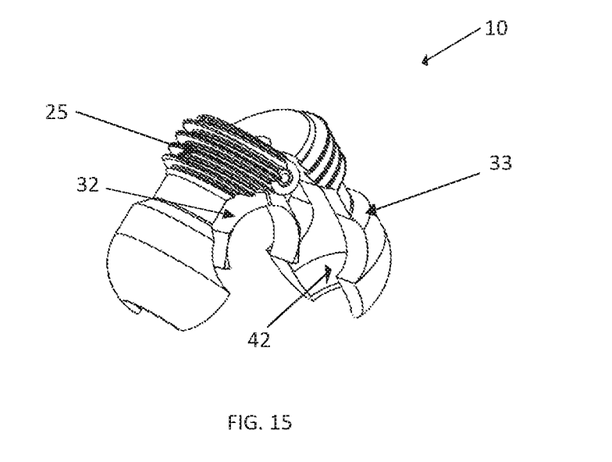
FIG. 15 is a perspective view of a threaded tulip head of a poly axial screw system, in accordance with an embodiment of the present invention.
Figure 16:
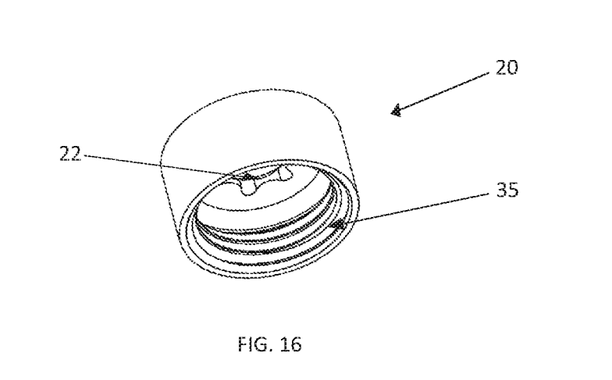
FIG. 16 is a bottom perspective view of a threaded tulip fastener, in accordance with an embodiment of the present invention.

As shown in FIGS. 7-8, in some embodiments, the exterior portion of the upper chamber 11 may include partial spiral wedged portions 19 and 21 having divots 23 and 24 at their respective ends. The wedged portions 19 and 21 may be deeper at the edge of the tulip head 33 and shallower at the middle of the tulip head 33. In an exemplary embodiment, the tulip fastener 20 is placed onto the tulip head 33 such that the locking protrusions 28 and 29 on the tulip fastener 20 may easily slide over the deeper portions or divots 23 and 24 of wedges 19 and 21. As the fastener 20 is twisted, the locking protrusions 28 and 29 become pressed against the shallow portions of the spiral wedges 19 and 21 to secure the tulip fastener 20 to the tulip head 33.

As shown in FIGS. 9-16, in some embodiments, the exterior portion of the upper chamber 11 includes a threaded portion 25, corresponding to a threaded portion along an interior portion of the tulip fastener 20.

According to an embodiment of the present invention, provided is a tulip head 33 comprising a first side 16 and a second side 26. The top portions of first side 16 and second side 26 collectively create the upper chamber 11, and the bottom portions of the first side 16 and the second side 26 collectively create the lower chamber 13. The interior portion of the lower chamber 13 contains a concave portion 42. The concave portion 42 may be adapted to receive a portion of the bone screw 12, for example, the ball head 34. Once the tulip fastener 20 is inserted in the unlocked position onto the tulip head 33, the concave portion 42 of the tulip is adapted to fit tightly onto a portion of the ball head 34, while still allowing for the tulip head 33 to rotate about the ball head 34. The tulip fastener 20 may be adapted to tightly hold the two sides 16 and 26 of the tulip head 33 such that the concave portion 42 forms a friction fit onto ball head 34. In some embodiments, the exterior portion of the upper chamber comprises a threaded portion. In an exemplary embodiment, the tulip fastener 20 is rotated or twisted about the threaded portion 24 of the tulip head 33, causing the bottom of the tulip fastener 20 to come into contact with the fusion rod 18. Upon continued pressing or twisting of the tulip fastener 20 on the fusion rod 18, the rod 18 is pushed out of the upper base 17 of the collet 32, and onto ball head 34 of the screw 12. This action secures the rod 18 into a locked position and tightens the interior concave portion 42 around the ball head 34. Thus, in the locked position (FIG. 6), the tulip head 33 is closed, with the concave portion 42 tightly fitting the ball head 34, and the fusion rod 18 held tightly between the tulip fastener 20 and the top of the ball head 34, with the fusion rod 18 stabilized horizontally by the saddle horns 14 and 15. In some embodiments, the ball head 34 may include a rim 36 to support a side of the fusion rod 18. In some embodiments, the ball head 34 may include a docking portion 38 to allow a screw assembly tool to grip the screw 12 during insertion of the screw into a desired bone (FIG. 3).

As shown in FIG. 8, the bottom portion of the tulip fastener 20 may be configured with locking protrusions 28 and 29 and a docking area 22 to allow a tulip assembly tool to grip the tulip fastener 20 during assembly of the tulip head 33 onto the ball head 34 and to achieve the closed position (FIGS. 1 and 6).

According to an embodiment of the present invention, provided is a poly axial screw system 10 as described herein wherein the tulip head 33 is primarily comprised of a rigid material, and wherein the tulip collet 32 is primarily comprised of a material of a lesser rigidity. In some embodiments, the tulip head 33 is made of a rigid material including one or more of cobalt-chrome, cobalt-chrome alloy, titanium, and titanium alloy. In some embodiments, the tulip head 33 is comprised of any combination of similarly suitable materials to achieve the desired rigidity.

According to an embodiment of the present invention, provided poly axial screw system 10 as described herein wherein the tulip head 33 is made of one or more of cobalt-chrome, and cobalt-chrome alloy, optionally coated with one or more of titanium and titanium alloy, and the tulip collet 32 is made of one or more of titanium and titanium alloy.

While multiple embodiments are disclosed, still other embodiments of the present invention will become apparent to those skilled in the art from this detailed description. There may be aspects of this invention that may be practiced without the implementation of some features as they are described. It should be understood that some details have not been described in detail in order to not unnecessarily obscure focus of the invention. The invention is capable of myriad modifications in various obvious aspects, all without departing from the spirit and scope of the present invention. It should be noted that the features illustrated in the drawings are not necessarily drawn to scale, and features of one embodiment may be employed with other embodiments as the skilled artisan would recognize, even if not explicitly stated herein. Accordingly, the drawings and descriptions are to be regarded as illustrative in nature and not restrictive.

The invention claimed is:

1. A tulip assembly comprising:
   a tulip head with a first side connected to a second side by a rotatable joint that enables said tulip head to pivot between an open and closed position; and
   a collet coupled to said tulip head and configured for supporting a fusion rod, wherein said collet is coupled to said tulip head via a hinge pin of said rotatable joint.

2. The tulip assembly of claim 1, wherein said collet comprises first and second saddle horns that correspond to said first and second sides of said tulip head and hold said fusion rod.

3. The tulip assembly of claim 1, further comprising a fastener adapted to engage with said tulip head and secure said tulip head in said closed position around said fusion rod and a head portion of a screw.

4. The tulip assembly of claim 3, wherein locking protrusions formed on said fastener engage with wedged portions formed on said tulip head.

5. The tulip assembly of claim 1, wherein said tulip head comprises an upper chamber that is adapted to retain said collet and a lower chamber that is configured to be closed around a head portion of a screw that is fixed in bone.

6. The tulip assembly of claim 1, wherein said fusion rod is supported by said collet in a position that is between said rotatable joint and a head portion of a screw to which said tulip assembly is attached.

7. A tulip assembly comprising:
   a tulip head comprising an upper chamber and a lower chamber each having a first and second side with edges that are shaped to define an opening passing entirely through a central side portion of said tulip head, wherein said opening is adapted to entirely enclose said fusion rod within said tulip head when said tulip head is pivoted to a closed position via a rotatable joint; and
   a collet coupled to said tulip head via a hinge pin of said rotatable joint, wherein said collet is retained within said upper chamber of said tulip head and configured to support said fusion rod within said opening.

8. The tulip assembly of claim 7, wherein said lower chamber of said tulip head is wider than said upper chamber of said tulip head.

9. The tulip assembly of claim 7, wherein an exterior portion of said upper chamber of said tulip head is configured to receive a fastener that secures said tulip head in said closed position.

10. The tulip assembly of claim 7, wherein said lower chamber is formed with a first side and a second side that close to define an interior concave portion that attaches around a screw head.

11. The tulip assembly of claim 7, wherein said lower chamber is formed with a concave inner portion that is adapted to engage with a screw head.

12. The tulip assembly of claim 7, wherein said rotatable hinge is positioned within a top portion of said upper chamber of said tulip head and configured to open and close said tulip head.

13. The tulip assembly of claim 7, wherein a top portion of said collet is formed with a hole through which said hinge pin intersects to couple said collet with said tulip head.

14. A tulip assembly comprising:
    a tulip head with a first and second side that are adapted to open and close via a hinge joint; and
    a collet that is formed with a base that connects to said tulip head via a hinge pin of said hinge joint and is further configured with a first and second saddle horn that are centered between and retained within said first and second side of said tulip head.

15. The tulip assembly of claim 14, wherein said first and second saddle horns of said collet form a U-shaped cradle that is open towards a screw head to which said tulip assembly attaches.

16. The tulip assembly of claim 14, wherein said collet is configured to support a fusion rod in a position that is between said hinge joint and a head portion of a screw to which said tulip assembly attaches.

17. The tulip assembly of claim 14, wherein said tulip head comprises an upper chamber that is adapted to retain said collet and a lower chamber that is wider than said upper chamber and is formed with a concave inner portion that is configured to surround and attach to a head portion of a screw.

18. The tulip assembly of claim 14, wherein said hinge joint is rotatable and configured to permit said first and second side of said tulip to open and close around said collet.

19. The tulip assembly of claim 14, wherein said tulip head is configured to first engage with fusion rod then attach to a head of a screw.

* * * * *